US011016158B2

(12) United States Patent
Paul et al.

(10) Patent No.: US 11,016,158 B2
(45) Date of Patent: May 25, 2021

(54) AUTOMATIC DETERMINATION OF CORRECTION FACTORS FOR A MAGNETIC RESONANCE SYSTEM (71) Applicant: Siemens Healthcare GmbH, Erlangen (DE)

(72) Inventors: Dominik Paul, Bubenreuth (DE); Mario Zeller, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 344 days.

(21) Appl. No.: 16/208,871

(22) Filed: Dec. 4, 2018

(65) Prior Publication Data
US 2019/0178965 A1 Jun. 13, 2019

(30) Foreign Application Priority Data
Dec. 11, 2017 (DE) .................. 102017222359.6

(51) Int. Cl.
G01R 33/54 (2006.01)
G01R 33/565 (2006.01)
G01R 33/56 (2006.01)
G01R 33/58 (2006.01)
G06T 1/00 (2006.01)
(Continued)

(52) U.S. Cl.
CPC ............ G01R 33/543 (2013.01); A61B 5/055 (2013.01); G01R 33/0029 (2013.01);
(Continued)

(58) Field of Classification Search
CPC ............ G01R 33/543; G01R 33/56572; G01R 33/5659; G01R 33/5608; G01R 33/58;
(Continued)

(56) References Cited

U.S. PATENT DOCUMENTS 8,854,037 B2 * 10/2014 Feiweier .......... G01R 33/56518
324/307
9,395,429 B2 7/2016 Grodzki
(Continued)

FOREIGN PATENT DOCUMENTS

DE 102010013605 A1 10/2011

OTHER PUBLICATIONS

German Office Action for German Application No. 10 2017 222 359.6 dated Apr. 11, 2020.
(Continued)

*Primary Examiner* — Kim Y Vu
*Assistant Examiner* — Molly Delaney
(74) *Attorney, Agent, or Firm* — Lempia Summerfield Katz LLC (57) ABSTRACT

The disclosure relates to the automatic determination of correction factor values for producing MR images using a magnetic resonance system. A plurality of MR images is produced, wherein each MR image is produced using parameters with parameter values and using correction factors with correction factor values. In order to produce the MR images, MR data of the same examination object is acquired under the same external boundary conditions. The MR images are evaluated automatically in respect of artifacts in the respective MR image, in order to determine the MR image with the least artifacts among the MR images. The correction factor values are determined as those correction factor values which have been used to produce the MR image with the least artifacts. The parameters determine a sequence, with which the MR data is acquired for producing the MR images. The correction factors reduce influences which influence the acquisition of the MR data.

19 Claims, 3 Drawing Sheets (51) Int. Cl.
*A61B 5/055* (2006.01)
*G01R 33/00* (2006.01)
(52) U.S. Cl.
CPC ..... *G01R 33/5608* (2013.01); *G01R 33/5659* (2013.01); *G01R 33/56572* (2013.01); *G01R 33/58* (2013.01); *G06T 1/00* (2013.01); *G01R 33/583* (2013.01); *G06T 2207/10088* (2013.01)
(58) Field of Classification Search
CPC .... G01R 33/0029; G01R 33/583; G06T 1/00; G06T 2207/10088; A61B 5/055
See application file for complete search history.

(56) References Cited

U.S. PATENT DOCUMENTS

| | | | |
|---|---|---|---|
| 9,482,731 B2 | 11/2016 | Grodzki | |
| 2011/0241679 A1 | 10/2011 | Feiweier | |
| 2013/0009641 A1* | 1/2013 | Hori | G01R 33/4818 |
| | | | 324/309 |
| 2018/0017652 A1* | 1/2018 | Ye | G01R 33/5608 |
| 2019/0178965 A1* | 6/2019 | Paul | G01R 33/0029 |
| 2019/0302211 A1* | 10/2019 | Cai | G01R 33/5673 |
| 2019/0370970 A1* | 12/2019 | Kim | G06T 7/254 |
| 2020/0018809 A1* | 1/2020 | Duijndam | G01R 33/4828 |

OTHER PUBLICATIONS

Porter, David A., and Robin M. Heidemann. "High resolution diffusion-weighted imaging using readout-segmented echo-planar imaging, parallel imaging and a two-dimensional navigator-based reacquisition." Magnetic Resonance in Medicine: An Official Journal of the International Society for Magnetic Resonance in Medicine 62.2 (2009): 468-475.

\* cited by examiner

FIG 2

AUTOMATIC DETERMINATION OF CORRECTION FACTORS FOR A MAGNETIC RESONANCE SYSTEM

The application claims the benefit of German Patent Application No. DE 10 2017 222 359.6, filed Dec. 11, 2017, which is hereby incorporated by reference in its entirety.

TECHNICAL FIELD

The present disclosure relates to the automatic determination of correction factor(s)/correction factor value(s), in order, with these correction factor(s)/correction factor value(s), to produce magnetic resonance (MR) images using a magnetic resonance system.

BACKGROUND

There are numerous MR imaging sequences which require specific correction factors in order to generate MR images with as few artifacts as possible. Examples of such sequences are: an Echo Planar Imaging (EPI) sequence segmented during read-out; a Readout Segmentation of Long Variable Echo trains (RESOLVE) sequence; and a Pointwise Encoding Time Reduction with radial Acquisition (PETRA) sequence, wherein applications of this PETRA sequence are known from U.S. Pat. No. 9,482,731 B2 or from U.S. Pat. No. 9,395,429 B2, for instance; or radial or spiral-shaped sequences.

Correction factors are understood here to refer to correction factors that are system-specific to the respective magnetic resonance system, with which constant influences that influence the acquisition of the MR data are reduced. These correction factors depend on the one hand on the magnetic resonance system (e.g., on the type of magnetic resonance system, on the configuration of the gradient coils and the magnet, in other words, on the exact configuration of the magnetic resonance system). On the other hand, the correction factors also depend on the site or point at which the magnetic resonance system is located. Calibration measurements have to be performed in order to determine the correction factors or more precisely the values for the correction factors.

By way of example, in accordance with the prior art, for a RESOLVE sequence for different parameters (e.g., parameters relating to the image orientation and the echo distance) with in each case different values for the correction factors, MR data of the same spherical phantom is acquired and corresponding MR images are reconstructed therefrom. These MR images are then evaluated manually and the values of the correction factors, which belong to the best evaluated image (e.g., the image with the least artifacts), are determined for the respective combination of parameter values and are permanently stored in the program code for this parameter value combination for the sequence. Correction factor values for parameter combinations which were not examined during the previously described calibration are interpolated as a function of the determined correction factor values.

By way of example, as a correction factor the RESOLVE sequence has a scaling factor for the read-out gradient amplitude, e.g., the amplitude to be used in each case for the read-out gradient is multiplied by this scaling factor. This scaling factor compensates for the fact that the read-out gradients are not exactly sinusoidal in the case of the RESOLVE sequence. In other words, this scaling factor provides that the previously viewed or calculated gradient moment is also generated exactly by the read-out gradient amplitudes determined by the sequence.

Aside from correction factors relating to the gradient moments, there are also correction factors which correct the time response. These correction factors provide that the feeding-in of a gradient or an RF pulse is artificially delayed or brought forward in order to compensate for corresponding timing inaccuracies.

The calibration or determination of the correction factor values according to the prior art is time-consuming and prone to error. Moreover, this manual determination of the correction factor values frequently has to be repeated if system hardware specifications (e.g., the design of gradient coils) change, which is frequently the case in the development phase.

SUMMARY AND DESCRIPTION

The scope of the present disclosure is defined solely by the appended claims and is not affected to any degree by the statements within this description. The present embodiments may obviate one or more of the drawbacks or limitations in the related art.

The object of the present disclosure is to speed up the determination of correction factors compared to the prior art.

According to the disclosure, this object is achieved by a method for automatically determining correction factor values for producing MR images by a magnetic resonance system, by a computer program product, or by an electronically readable data carrier.

A method is disclosed for automatically determining correction factor values for producing MR images with the aid of a magnetic resonance system. Here, the method includes producing a number of MR images of the same examination object or phantom. In this act, a number of MR images is produced for a specific combination of parameters, e.g., for a specific assignment of the parameters with parameter values. To this end, each of these MR images is produced with an individual assignment of correction factors with correction factor values. More precisely, MR data of the examination object is acquired by a sequence, which is defined by the corresponding parameter values, in order to reconstruct the respective MR image on the basis of this MR data. To this end, when the MR data is acquired, different correction factor value combinations (e.g., different assignments of the correction factors with correction factor values) are used for the specific parameter value combination so that a number of MR data records and therefore a number of MR images are produced for each parameter value combination.

The method further includes automatically evaluating the MR images with respect to artifacts in the respective MR image, in order to determine the most artifact-free MR image (e.g., the MR image with the least artifacts) within the MR images produced. In this act, the most artifact-free MR image is therefore determined automatically for the specific parameter value combination.

The method further includes determining the correction factor values as those correction factor values which have been used to create the most artifact-free MR image. In this act, the correction factor values are therefore determined, which have been used in the act of producing MR images for the purpose of producing the most artifact-free image of the specific parameter value combination.

This evaluation with respect to artifacts is advantageously reproducible by, in particular, the evaluation of the MR images being carried out automatically. Furthermore, the automatic evaluation of the MR images produces improved results and speeds up the determination of the correction factors compared with the prior art, according to which a manual evaluation is used. As a result, the method achieves the afore-cited object. As explained in more detail below, the following procedures exist for automatically evaluating the MR images in respect of artifacts: (1) evaluation of the MR images as a function of a first derivation of pixel values of the respective MR image to be evaluated; (2) evaluation of the MR images as a function of Fourier coefficients, which were determined by an inverse discrete Fourier transform for pixel values of the respective MR image to be evaluated; (3) evaluation of the MR images based on a similarity analysis of the respective MR image to be evaluated with a reference image; and/or (4) evaluation of the MR images based on machine learning.

As already explained above, according to a first embodiment, the MR images are evaluated automatically as a function of the first derivation of pixel values of the respective MR image to be evaluated. To this end, the first derivation of pixel values which exist along a predetermined direction (e.g., in the read-out direction or in the phase encoding direction) in the MR image to be evaluated, is calculated in order to calculate derivation values by this calculation. Here, the first derivation of pixel values is understood to refer to the difference in values of two adjacent pixels. For instance, the first derivation f'(x) may be determined on the basis of the following equation (1) for 0<x<N.

$$f'(x) = PW(x+1) - PW(x) \qquad (1)$$

Here, PW(x) corresponds to the pixel value at the x'th point in the MR image and N corresponds to the number of pixels along the predetermined direction. If 128 pixels are acquired along the read-out direction (or for each line), for instance, 127 derivation values are calculated for each line. A total value is determined as a function of the derivation values calculated in the MR image. Of the MR images to be evaluated, the MR image in which this total value has the smallest value is determined as the most artifact-free MR image.

Instead of calculating the first derivation along the predetermined direction, with the first embodiment the first derivation of pixel values may also be calculated in a number of directions (e.g., in the read-out direction and phase encoding direction), e.g., using a gradient operator or Nabla operator. The result is then, in particular, a vector field, which may be analyzed for a particular direction, for instance, or on the basis of an amplitude of the vectors of the field. As a function of this analysis, a value comparable with the total value may be determined, as a function of which the most artifact-free MR image may then be determined.

An artifact is frequently characterized by a sharp transition being present in the MR image, which then results in a high derivation value. The previously described embodiment therefore advantageously represents a good potential for specifying, on the basis of the total value (or one value as a function of the derivation values), a measure of contamination by artifacts in an MR image.

In order to determine the total value, all derivation values may on the one hand be added together. Another possibility includes only determining the M largest derivation values and in adding them together for the purpose of determining the total value. Here, M may be significantly smaller than the number of derivation values determined for the MR image to be evaluated. For instance, M may correspond to one tenth of the determined derivation values.

For automatically evaluating the MR images on the basis of the derivation values, the derivation values may be calculated, for instance, for all lines (or columns) of the MR images to be evaluated. It is also possible, however, to determine the derivation values just for specific lines or columns of the MR images to be evaluated, for instance, for a specific number of lines or columns in the center of the respective MR image. Furthermore, the derivation values (and therefore the total values) may also only be determined for one line or column, for instance for the line or column in the center of the MR image.

According to the previously described second embodiment, the automatic evaluation of the MR images takes place with the aid of Fourier coefficients. To this end, an inverse discrete Fourier transformation is carried out, in order as a result to obtain the Fourier coefficients, on the basis of the pixel values of the MR image to be evaluated, which run along a predetermined direction (e.g., the read-out direction or phase encoding direction). A total value is determined as a function of these Fourier coefficients. Of the MR images to be evaluated, the MR image in which this total value has the smallest value is determined as the most artifact-free MR image.

In order to determine the total value, all Fourier coefficients outside of what is known as the main lobe may be added together for instance for all lines or columns for which the Fourier coefficients have been determined. Here, in addition to the coefficient with the largest value, the main lobe includes all coefficients up to and including the first (relative) minimum. With Fourier coefficients which are mirror-symmetrical to the main lobe, in addition to the coefficient with the largest value, the main lobe includes all coefficients up to and including the two first (relative) minima arranged in mirror symmetry with one another.

In a similar manner to the first embodiment, with the second embodiment, it is possible to determine the Fourier coefficients not for all lines or columns, but instead in the same way as in the first embodiment just for specific lines or columns or also just for one line or column. In this case, the total value is also only calculated as a function of those Fourier coefficients which have actually been determined for the MR image to be evaluated or lie in the corresponding line or column.

If the Fourier coefficients are calculated for instance by an inverse Fourier transformation on the basis of pixel values, the number of calculated Fourier coefficients corresponds to the number of pixel values from which the Fourier coefficients have been determined.

The Fourier coefficients represent a measure of energy present in the respective MR image. The further this energy manifests itself in the Fourier coefficients outside of the main lobe, the more artifacts the MR image has. The previously described total value therefore corresponds advantageously to a measure of the extent of artifacts in the MR image to be evaluated.

According to the previously described third embodiment, the evaluation of the MR images takes place with the aid of a similarity analysis. To this end, an image registration for each of the MR images to be evaluated is carried out with a reference image, which maps the examination object or phantom in an artifact-free manner (as far as possible). A similarity analysis between the MR image to be evaluated in each case and this reference image is then carried out. The MR image among the MR images to be evaluated, which has the greatest similarity to the reference image pursuant to the similarity analysis, is determined as the most artifact-free MR image.

The evaluation of the MR images with the aid of the similarity analysis may be carried out for instance with a trans-information or mutual information, which specifies the strength of the statistical association between two random variables. Normalized variants of the trans-information or mutual information may also be used here. Differential search algorithms or a particle swarm optimization may also be used for the similarity analysis.

The evaluation of the MR images with the aid of the similarity analysis is advantageously not dependent on the properties of specific artifact types and may therefore be used advantageously for any calibration problem.

According to the fourth embodiment, the automatic evaluation takes place by machine learning. To this end, a conventional algorithm for machine learning or deep learning, which has been trained beforehand on the basis of optimal (e.g., artifact-free) MR images and non-optimal MR images (e.g., provided with artifacts), is used to evaluate the MR images, for instance. This algorithm or this procedure is then applied to the MR images to be evaluated, in order to determine the most artifact-free MR image from among these MR images.

In accordance with the disclosure, neural networks, (in particular what are known as Hopfield networks), which are trained beforehand on the basis of optimal and non-optimal MR images, may be used for this purpose.

Within the scope of the present disclosure, a magnetic resonance system is also provided in order thus to determine correction factor values automatically for the purpose of producing MR images. In such cases the magnetic resonance system includes an RF control unit, a gradient control unit, an image sequence controller, and a computing unit. The magnetic resonance system is configured to produce a number of MR images with the aid of the RF control unit, the gradient control unit, the image sequence controller, and the computing unit. In order to produce the MR images, the magnetic resonance system acquires MR data of the same examination object or phantom under the same external boundary conditions. A number of MR images is produced here for each assignment of the parameters with parameter values, wherein other correction factor values are used for data acquisition for the respective MR image. The magnetic resonance system is configured to evaluate the MR images produced with respect to artifacts, in order, on the basis of this evaluation, to determine the MR image with the least artifacts among the MR images. Furthermore, the magnetic resonance system is configured to determine those correction factor values, which have been used to produce the MR image with the least artifacts, as the correction factor values to be determined for the respective parameter value combination.

The advantages of the magnetic resonance system correspond substantially to the advantages of the method, which have been described above in detail and are therefore not repeated here.

The present disclosure further describes a computer program product, (e.g., an item of software), which may be loaded into a memory store of a programmable control device or a computing unit of a magnetic resonance system. With this computer program product, all or various of the above-described embodiments of the method may be carried out when the computer program product runs in the control device. Here the computer program may require programming code or modules, (e.g., libraries and auxiliary functions), in order to realize the corresponding embodiments of the method. In other words, an item of software in particular is to be protected by the computer program product, with which one of the above-described embodiments of the method may be carried out or which carries out this embodiment. Herein, the software may be a source code (e.g., C++) which is compiled and bound or which is only interpreted, or is an executable software code which, for execution, need only be loaded into the corresponding computing unit or control device.

Finally, the present disclosure provides an electronically readable data carrier, (e.g., a DVD, a magnetic tape, a hard disk, or a USB stick), on which electronically readable control information such as software (cf. above), is stored. When this control information (e.g., software) is read from the data carrier and stored in a control device or computing unit of a magnetic resonance system, all the embodiments of the above-described method may be carried out.

With the present disclosure, correction factor values may advantageously be determined automatically for any sequences. This includes both any gradient echo sequences and also any spin echo sequences and also sequences for single-point acquisition. Of sole importance here is that the influences or properties to be eliminated with the correction factors are not of a random nature.

BRIEF DESCRIPTION OF THE DRAWINGS

The present disclosure will be described in detail below using embodiments making reference to the drawings.

DETAILED DESCRIPTION

Figure 1:
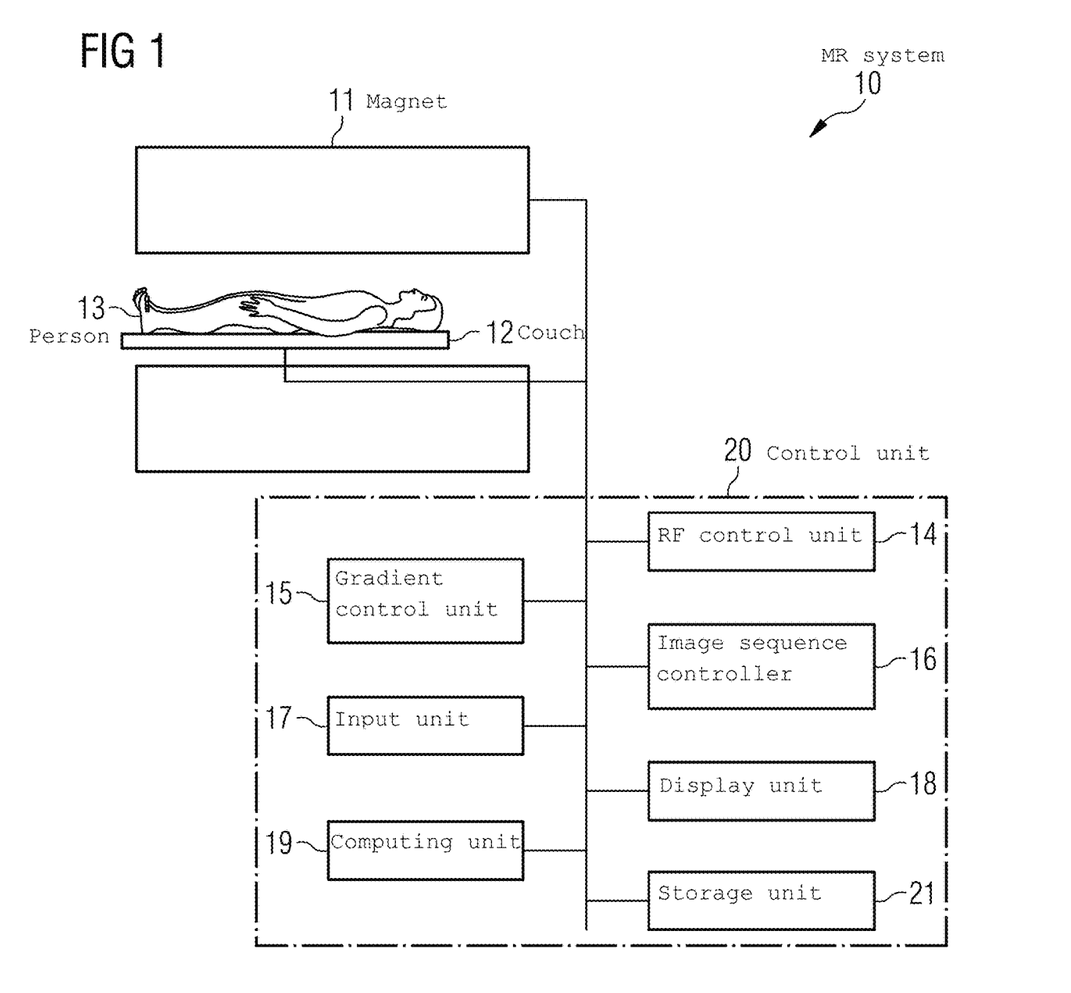
FIG. 1 represents an example of a magnetic resonance system.

With reference to FIG. 1, a magnetic resonance system 10 is shown, with which, as described below, correction factor values are determined automatically. The magnetic resonance system 10 has a magnet 11 for generating a polarization field BO, wherein a person 13 being examined arranged on a couch 12 is moved into the magnet 11, in order to record spatially encoded magnetic resonance signals or MR data from the person 13 being examined there. The coils used for signal recording, such as a whole-body coil or local coils, are not shown for reasons of clarity. By irradiating high frequency coils and switching magnetic field gradients, the magnetization generated by the polarization field BO is deflected out of the equilibrium position and spatially encoded and the resultant magnetization is detected by the receiving coils. How MR images may be generated by irradiating RF pulses and switching magnetic field gradients in different combinations and sequences is in principle known to a person skilled in the art and will not be explained in greater detail here.

The magnetic resonance system 10 also has a control unit 20 (e.g., including one or more processors) which may be used for controlling the magnetic resonance system 10. The controller 20 has a gradient control unit 15 for controlling and switching the necessary magnetic field gradients. An RF control unit 14 is provided for controlling and generating the RF pulses for deflecting the magnetization. An image sequence controller 16 controls the sequence of magnetic field gradients and RF pulses and thus indirectly the gradient control unit 15 and the RF control unit 14. The gradient control unit 15, the RF control unit 14, and/or the image sequence controller 16 may be formed by one or more processors. An operator may control the magnetic resonance system 10 by way of an input unit 17, and MR images and other information required for control purposes may be displayed on a display unit 18. A computing unit 19 with at least one processor unit (e.g., one or more processors; not shown) is provided for controlling the different units in the control unit 20 and for carrying out computing operations. Furthermore, a storage unit 21 is provided in which, for example, program modules or programs may be stored which, when they are executed by the computing unit 19 or its processor unit, may control the sequence of actions of the magnetic resonance system 10. The computing unit 19 is embodied to calculate the MR images from the acquired MR signals.

Figure 2:
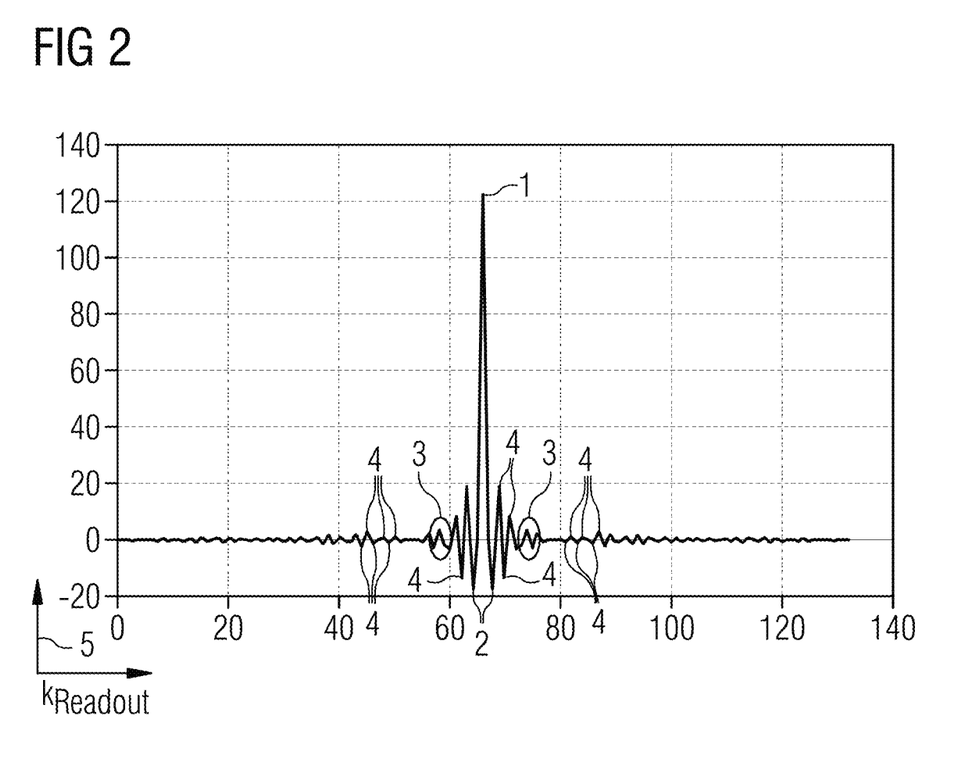
FIG. 2 represents Fourier coefficients calculated within the scope of an embodiment.

FIG. 2 shows Fourier coefficients 1-4 which have been calculated with an inverse discrete Fourier transformation on the basis of 128 pixel values in the read-out direction. It may be seen that the Fourier coefficient 1 with the largest value is in the center. The Fourier coefficients 2, which represent the two first relative minima, are located to the right and left (in the in $k_{Readout}$ direction) adjacent to this Fourier coefficient 1. Further, Fourier coefficients are identified with the reference character 4. With the two ellipses identified with the reference character 3, it should be made clear that the Fourier coefficients shown in FIG. 2 are in mirror symmetry with the position of the Fourier coefficient 1.

The Fourier coefficients of the main lobe are eliminated in order to determine a total value of the Fourier coefficients shown in FIG. 2. These Fourier coefficients of the main lobe include the Fourier coefficient 1 with the largest value in the center, the two Fourier coefficients 2 which correspond to the two first relative minima, and the Fourier coefficients lying between these two Fourier coefficients 2. The remaining Fourier coefficients (e.g., all Fourier coefficients outside of the Fourier coefficients of the main lobe) are added up with respect to their amplitude value 5 for the purpose of determining the total value.

Figure 3:
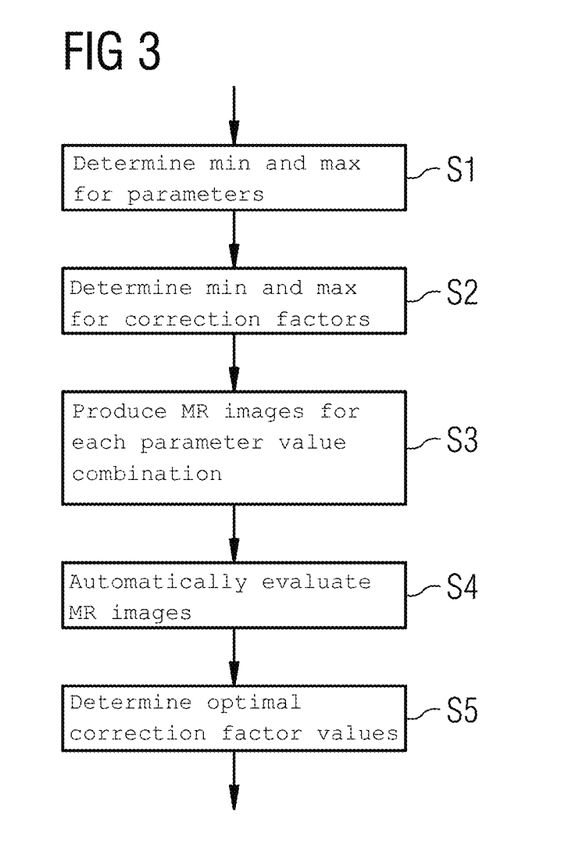
FIG. 3 depicts the flow chart of an exemplary procedure for determining correction factor values.

FIG. 3 depicts the flow chart of a method for automatically determining correction factor values.

In act S1, for a quantity of parameters, a minimum and a maximum are determined or prespecified for each parameter. In act S2, for a quantity of correction factors, a minimum and a maximum are similarly determined or prespecified for each correction factor. It should be explicitly noted here that both the quantity of parameters and also the quantity of correction factors may also include just one parameter or one correction factor.

Act S3 is executed for all possible combinations of parameter values. Assuming that n parameters exist and according to a simplified example m parameter values from the corresponding minimum up to the corresponding maximum exist for each parameter, then $m^n$ parameter value combinations exist. However, a varying number of possible parameter values may exist for two parameters. Furthermore, it is also possible for the quantity of parameter value combinations, for which the correction factor values are to be determined in each case, to be predetermined in another way, without a minimum and maximum being predetermined for each parameter.

A number of MR images is produced in act S3 for each parameter value combination, wherein each of these MR images is produced with a different correction factor value combination. In other words, MR data of the same phantom is detected repeatedly for each parameter value combination, wherein a different correction factor value combination is used in each case. MR images are reconstructed as a function of the detected MR data so that a number of MR images is produced for the respective parameter value combination.

The MR images are evaluated automatically in act S4, in order automatically to identify the MR image from the quantity of MR images produced for the respective parameter value combination, which has the least artifacts. On the basis of this most artifact-free MR image, the optimal correction factor values are then determined in act S5 for the respective parameter combination. These optimal correction factor values correspond to those correction factor values that have been used for the respective parameter value combination when acquiring the MR data, from which the MR image that has been estimated as the most artifact-free MR image has then been reconstructed. In one embodiment, MR images are generated by the magnetic resonance system using the optimal correction factor values determined in act S5.

Although the disclosure has been illustrated and described in detail by the exemplary embodiments, the disclosure is not restricted by the disclosed examples and the person skilled in the art may derive other variations from this without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for automatically determining correction factor values for producing magnetic resonance (MR) images using a magnetic resonance system, the method comprising:
 producing a plurality of MR images, wherein each MR image of the plurality of MR images is produced using parameters with parameter values and using correction factors with correction factor values, wherein MR data for producing the plurality of MR images of a same examination object is acquired under same external boundary conditions;
 determining an MR image with the least artifacts among the plurality of MR images, wherein the determining of the MR image with the least artifacts among the plurality of MR images comprises automatically evaluating the plurality of MR images with respect to artifacts in the respective MR image; and
 determining the correction factor values, wherein the determining of the correction factor values comprises using the correction factor values that have been used to produce the MR image with the least artifacts as the correction factor values,
 wherein the parameters determine a sequence, with which the MR data is acquired for producing the MR images,
 wherein the correction factors reduce influences that influence the acquisition of the MR data.

2. The method of claim 1, wherein the automatically evaluating of the plurality of MR images comprises:
- calculating, for each MR image of the plurality of MR images, first derivation of pixel values present along a predetermined direction in the respective MR image;
- determining, for each MR image of the plurality of MR images, a total value as a function of the calculated first derivation of pixel values; and
- determining the MR image of the plurality of MR images as the MR image with the least artifacts, in which the total value is smallest.

3. The method of claim 2, wherein the total value is determined as a total of all first derivation of pixel values.

4. The method of claim 2, wherein the total value is determined as a sum of M largest first derivation of pixel values within the calculated first derivation of pixel values, and
wherein M is a predetermined natural number.

5. The method of claim 1, wherein automatically evaluating the plurality of MR images comprises:
- executing an inverse discrete Fourier transformation for pixel values present along a predetermined direction in the MR image to be evaluated in each case, in order to obtain Fourier coefficients;
- determining a total value as a function of the Fourier coefficients; and
- determining the MR image of the plurality of MR images as the MR image with the least artifacts, in which the total value is smallest.

6. The method of claim 5, wherein the total value is determined as a sum of all Fourier coefficients outside of a main lobe of the Fourier coefficients.

7. The method of claim 1, wherein the automatically evaluating the plurality of MR images comprises:
- carrying out an image registration for each MR image of the plurality of MR images with a reference image;
- carrying out a similarity analysis between the MR image to be evaluated in each case and the reference image; and
- determining the MR image of the plurality of MR images as the MR image with the least artifacts, in which the similarity analysis has determined a greatest similarity with the reference image.

8. The method of claim 1, wherein the automatically evaluating of the plurality of MR images comprises:
- determining, based on a procedure, the MR image with the least artifacts among the plurality of MR images, the procedure having been trained using machine learning based on optimal and non-optimal MR images.

9. A magnetic resonance system configured to automatically determine correction factor values for producing magnetic resonance (MR) images, wherein the magnetic resonance system comprises:
- an RF control unit;
- a gradient control unit;
- an image sequence controller; and
- a computing unit,
- wherein the magnetic resonance system is configured to produce a plurality of MR images by the RF control unit, the gradient control unit, the image sequence controller, and the computing unit,
- wherein the magnetic resonance system is further configured to produce each MR image of the plurality of MR images using parameters of parameter values and using correction factors with correction factor values,
- wherein the magnetic resonance system is further configured to acquire MR data for producing the plurality of MR images of a same examination object under same external boundary conditions,
- wherein the magnetic resonance system is further configured to determine an MR image with least artifacts among the plurality of MR images, wherein the determination of the MR image with the least artifacts comprises evaluation of the plurality of MR images with respect to artifacts in the respective MR image,
- wherein the magnetic resonance system is further configured to determine the correction factor values, wherein the determination of the correction factor values comprises use of the correction factor values that have been used to produce the MR image with the least artifacts as the correction factor values,
- wherein the parameters determine a sequence with which the MR data is acquired for producing the MR images, and
- wherein the correction factors are configured to reduce influences that influence the acquisition of the MR data.

10. The magnetic resonance system of claim 9, wherein the magnetic resonance system is configured to:
- calculate, for each MR image of the plurality of MR images, first derivation of pixel values present along a predetermined direction in the respective MR image;
- determine, for each MR image of the plurality of MR images, a total value as a function of the calculated first derivation of pixel values; and
- determine the MR image of the plurality of MR images as the MR image with the least artifacts, in which the total value is smallest.

11. The magnetic resonance system of claim 9, wherein the evaluation of the plurality of MR images comprises:
- execution of an inverse discrete Fourier transformation for pixel values present along a predetermined direction in the MR image to be evaluated in each case, in order to obtain Fourier coefficients;
- determination of a total value as a function of the Fourier coefficients; and
- determination of the MR image of the plurality of MR images as the MR image with the least artifacts, in which the total value is smallest.

12. The magnetic resonance system of claim 9, wherein the evaluation of the plurality of MR images comprises:
- carry out of an image registration for each MR image of the plurality of MR images with a reference image;
- carry out of a similarity analysis between the MR image to be evaluated in each case and the reference image; and
- determination of the MR image of the plurality of MR images as the MR image with the least artifacts, in which the similarity analysis has determined a greatest similarity with the reference image.

13. The magnetic resonance system of claim 9, wherein the magnetic resonance system is further configured to:
- use a procedure, which has been trained using machine learning based on optimal and non-optimal MR images, in order to determine, based on the procedure, the MR image with the least artifacts among the plurality of MR images.

14. In a non-transitory computer-readable storage medium that stores instructions executable by a controller of a magnetic resonance system to automatically determine correction factor values for producing magnetic resonance (MR) images using the magnetic resonance system, the instructions comprising:
- producing a plurality of MR images, wherein each MR image of the plurality of MR images is produced using parameters with parameter values and using correction factors with correction factor values, wherein MR data for producing the plurality of MR images of a same examination object is acquired under same external boundary conditions;

determining an MR image with the least artifacts among the plurality of MR images, the determining of the MR image with the least artifacts among the plurality of MR images comprising automatically evaluating the plurality of MR images with respect to artifacts in the respective MR image; and determining the correction factor values, wherein the determining of the correction factor values comprises using the correction factor values that have been used to produce the MR image with the least artifacts as the correction factor values, wherein the parameters determine a sequence, with which the MR data is acquired for producing the MR images, wherein the correction factors reduce influences that influence the acquisition of the MR data.

15. The non-transitory computer-readable storage medium of claim 14, wherein automatically evaluating the plurality of MR images comprises:

calculating, for each MR image of the plurality of MR images, first derivation of pixel values present along a predetermined direction in the respective MR image;

determining, for each MR image of the plurality of MR images, a total value as a function of the calculated first derivation of pixel values; and determining the MR image of the plurality of MR images as the MR image with the least artifacts, in which the total value is smallest.

16. The non-transitory computer-readable storage medium of claim 15, wherein the total value is determined as a total of all first derivation of pixel values.

17. The non-transitory computer-readable storage medium of claim 15, wherein the total value is determined as a sum of M largest first derivation of pixel values within the calculated first derivation of pixel values, and wherein M is a predetermined natural number.

18. The non-transitory computer-readable storage medium of claim 14, wherein automatically evaluating the plurality of MR images comprises:

executing an inverse discrete Fourier transformation for pixel values present along a predetermined direction in the MR image to be evaluated in each case, in order to obtain Fourier coefficients;

determining a total value as a function of the Fourier coefficients; and determining the MR image of the plurality of MR images as the MR image with the least artifacts, in which the total value is smallest.

19. The non-transitory computer-readable storage medium of claim 18, wherein the total value is determined as a sum of all Fourier coefficients outside of a main lobe of the Fourier coefficients.

\* \* \* \* \*